(12) United States Patent
Soza et al.

(10) Patent No.: US 11,367,523 B2
(45) Date of Patent: Jun. 21, 2022

(54) METHOD FOR IMAGE DATA PROCESSING

(71) Applicant: Siemens Healthcare GmbH, Erlangen (DE)

(72) Inventors: Grzegorz Soza, Heroldsberg (DE); Stefan Grosskopf, Nuremberg (DE); Hannes Martinke, Magdeburg (DE); Christian Petry, Langensendelbach (DE); Helmut Ringl, Schwechat (AT); Michael Suehling, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 57 days.

(21) Appl. No.: 15/980,803

(22) Filed: May 16, 2018

(65) Prior Publication Data

US 2018/0336966 A1 Nov. 22, 2018

(30) Foreign Application Priority Data

May 19, 2017 (EP) ..................... 17172037

(51) Int. Cl.
*G16H 30/40* (2018.01)
*G06T 3/00* (2006.01)
(Continued)

(52) U.S. Cl.
CPC ........... *G16H 30/40* (2018.01); *G06T 3/0037* (2013.01); *G06T 11/003* (2013.01); *G06T 15/08* (2013.01);
(Continued)

(58) Field of Classification Search
CPC ... G06T 3/0037; G06T 15/08; G06T 2210/41; G06T 2207/30008; G06T 11/003;
(Continued)

(56) References Cited

U.S. PATENT DOCUMENTS 9,020,233 B2 4/2015 Liu et al.
9,547,906 B2 1/2017 El-Zehiry et al.
(Continued)

FOREIGN PATENT DOCUMENTS

WO WO 2006000925 A2 1/2006
WO WO-2012037091 A1 3/2012

OTHER PUBLICATIONS

Advanced Bone Visualization, Martinke, Mar. 2017 http://www.vismd.de/lib/exe/fetch.php?media=files:misc:martinke2017.pdf (Year: 2017).*

(Continued)

*Primary Examiner* — Jianxun Yang
(74) *Attorney, Agent, or Firm* — Harness, Dickey & Pierce, P.L.C.

(57) ABSTRACT

A method is for image data processing. In an embodiment, the method includes providing a 3D medical image data record, which relates to an elongated anatomical structure, a center line of the elongated anatomical structure being defined in the 3D medical image data record; defining at least one curved slice in the 3D medical image data record, the at least one curved slice winding around the center line; scanning at least one part of the 3D medical image data record into the at least one curved slice; and unrolling the at least one curved slice, into which the at least one part of the 3D medical image data record was scanned, at least one unrolled flat slice being determined. An image data processing unit is also for image data processing and a medical imaging apparatus includes the image data processing unit.

22 Claims, 9 Drawing Sheets

(51) Int. Cl.
*G06T 15/08* (2011.01)
*G06T 11/00* (2006.01)

(52) U.S. Cl.
CPC .......... *G06T 2207/30008* (2013.01); *G06T 2210/41* (2013.01); *G06T 2215/06* (2013.01)

(58) Field of Classification Search
CPC ...... G06T 2215/06; G16H 30/40; G06K 9/00; G06K 9/48; G06K 9/62
See application file for complete search history.

(56) References Cited

U.S. PATENT DOCUMENTS

| | | | |
|---|---|---|---|
| 9,558,568 B2 | 1/2017 | Kretschmer et al. | |
| 2007/0120845 A1* | 5/2007 | Matsumoto | G06T 15/08 345/419 |
| 2008/0055308 A1* | 3/2008 | Dekel | G06T 15/08 345/421 |
| 2010/0142788 A1 | 6/2010 | Matsumoto | |
| 2013/0007099 A1 | 1/2013 | Lee | |
| 2013/0070996 A1* | 3/2013 | Liu | G06K 9/00 382/131 |
| 2013/0272594 A1* | 10/2013 | Zelzer | G06T 11/008 382/131 |

OTHER PUBLICATIONS

X-ray CT for virtually unrolling damaged papyri, Allegra et al, 2016 https://link.springer.com/article/10.1007/s00339-016-9796-1 (Year: 2016).*

Ringl Helmut et al: "The ribs unfolded—a CT visualization algorithm for fast detection of rib fractures: effect on sensitivity and specificity in trauma patients"; European Radiology; Bd. 25 Nr. 7; pp. 1865-1874; XP055225320; DE; ISSN: 0938-7994; DOI: 10.1007/S00330-015-3598-2.

Martinke Hannes: "Advanced Bone Visualization Bachelor—Thesis in Study Computer Visualistics"; FP-V; pp. 1-71; XP002774431; Magdeburg.

European Search Report for European Application No. EP17172037 dated Oct. 6, 2017.

Miao H. et al.: "Placenta Maps: In Utero Placental Health Assessment of the Human Fetus", IEEE Transactions on Visualization and Computer Graphics, vol. 23, No. 6, Jun. 2017, Published. Feb. 24, 2017.

Kanitsar, Armin et al:; "Diagnostic Relevant Visualization of Vascular Structures"; Scientific Visualization: The Visual Extraction of Knowledge from Data; Springer; pp. 207-228; ISBN: 978-3-540-26066-0; DOI: 10.1007/3-540-30790-7_13; https://citeseerx.ist.psu.edu/viewdoc/download?doi=10.1.1.147.3356&rep=rep1&type=pdf; 2006.

Mistelbauer G. et al.: "Vessel Visualization using Curvicircular Feature Aggregation", Eurographics Conference on Visualization (EuroVis) 2013, vol. 32 (2013), No. 3; pp. 231-240.

Martinke H. et al.: "Bone Fracture and Lesion Assessment using Shape-Adaptive Unfolding", Eurographics Workshop on Visual Computing for Biology and Medicine (2017), published: Sep. 7, 2017.

Shin, Byeong-Seok et al:; "Efficient unfolding of virtual endoscopy using linear ray interpolation"; Computer Methods and Programs in Biomedicine; Elsevier; vol. 93; No. 2; pp. 174-184; ISSN: 0169-2607; DOI: 10.1016/J.CMPB.2008.09.003; XP025770037; 2009.

European Search Report for European Application No. 17172037.8, dated May 25, 2021.

* cited by examiner

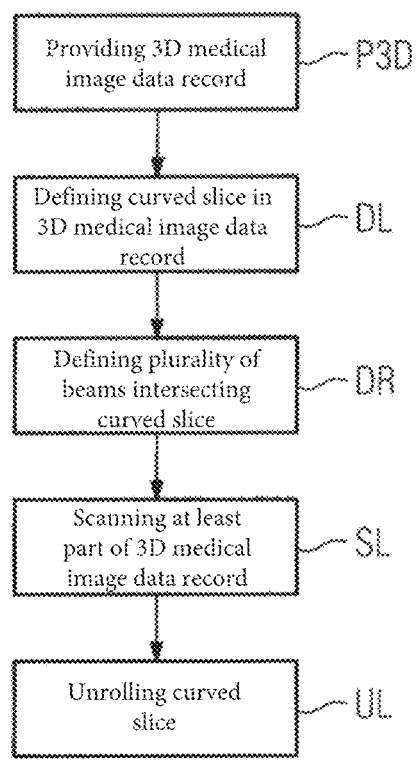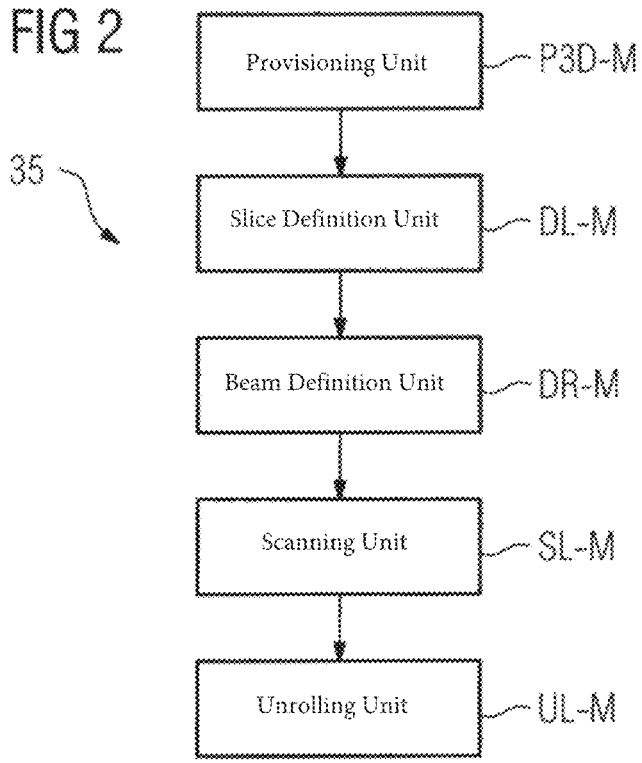

METHOD FOR IMAGE DATA PROCESSING

PRIORITY STATEMENT

The present application hereby claims priority under 35 U.S.C. § 119 to European patent application number EP 17172037.8 filed May 19, 2017, the entire contents of which are hereby incorporated herein by reference.

FIELD

At least one embodiment of the invention relates to a method for image data processing, an image data processing unit and a medical imaging apparatus.

BACKGROUND

After carrying out a medical imaging examination, for instance a CT scan, the image data is generally assessed by the attending radiologist at a diagnosis workstation. Diagnosis of the ribs on the basis of CT image data is often only possible for the attending radiologist with significant effort using current methods. In order to diagnose rib fractures for instance, the radiologist can either navigate through the slice data produced on the scanner or use a special software solution, which unfolds ribs, with the aid of the rib center lines determined from the image data, into a flat plane. In particular, the diagnosis of the curved ribs on conventional flat CT images, for instance on the basis of 300 to 400 images per patient, can be very laborious.

Visualization software exists, which allows the ribs unfolded into flat planes to be assessed. The unfolding of the ribs into a flat plane is known to the person skilled in the art in particular under the term "rib unfolding". A known software solution for this purpose is syngo.CT Bone Reading. These unfolded ribs form a 3D image data record and are typically visualized along flat sectional planes, so that further interaction steps are generally required for diagnosis.

U.S. Pat. No. 9,020,233 B2 discloses a method for extracting a center line of a rib in a 3D medical image data record.

U.S. Pat. No. 9,547,906 B2 discloses a method for correcting a center line of a rib, which has been extracted from a medical 3D image data record.

U.S. Pat. No. 9,558,568 B2 discloses a method for visualizing a skeleton with a plurality of bones.

SUMMARY

The inventors have discovered that with conventional rib unfolding, it is necessary to interactively adjust visualization parameters and navigate through 3D slice images, since only one single cut through the ribs is generally visible in the unfolded view.

At least one embodiment of the invention allows an improved representation of elongated anatomical structures, in particular ribs, in a medical image.

Further advantageous embodiments of the invention are taken into account in the claims.

At least one embodiment of the invention relates to a method for image data processing, wherein the method comprising:

providing a 3D medical image data record, which relates to an elongated anatomical structure, wherein a center line of the elongated anatomical structure is defined in the 3D medical image data record, defining at least one curved slice in the 3D medical image data record, wherein the at least one curved slice winds around the center line of the elongated anatomical structure, scanning at least one part of the 3D medical image data record into the at least one curved slice on the basis of the plurality of beams, and unrolling the at least one curved slice, into which the at least one part of the 3D medical image data record has been scanned, wherein at least one unrolled flat slice is determined.

At least one embodiment of the invention also relates to an image data processing unit, comprising:

a provisioning unit, which is embodied to provide a 3D medical image data record, which relates to an elongated anatomical structure, wherein a center line of the elongated anatomical structure is defined in the 3D medical image data record, a slice definition unit, which is embodied to define at least one curved slice in the 3D medical image data record, wherein the at least one curved slice winds around the center line of the elongated anatomical structure, a beam definition unit, which is embodied to define a plurality of beams, which each run radially with respect to the center line of the elongated anatomical structure and which intersect the at least one curved slice, a scanning unit, which is embodied to scan at least one part of the 3D medical image data record into the at least one curved slice on the basis of the plurality of beams, and an unrolling unit, which is embodied to unroll the at least one curved slice, into which the at least one part of the 3D medical image data record has been scanned, wherein at least one unrolled flat slice is determined.

At least one embodiment of the invention also relates to a medical imaging apparatus, having the image data processing unit.

At least one embodiment of the invention further relates to a non-transitory computer program product with a computer program, which can be loaded directly into a storage facility of an image data processing unit of a medical imaging apparatus, having program portions, in order to execute all the steps of an inventive method when the computer program is executed in the image data processing unit of the medical imaging apparatus.

At least one embodiment of the invention further relates to a non-transitory computer-readable medium, on which program portions which can be read in and executed by a computer are stored, in order to execute all steps of an inventive method when the program portions are executed by the computer.

BRIEF DESCRIPTION OF THE DRAWINGS

The invention is explained below using example embodiments with reference to the accompanying figures. The illustration in the figures is schematic, greatly simplified and not necessarily to scale.

In the drawings:

FIG. 1 shows a block diagram of an example embodiment of an inventive method for image data processing, FIG. 2 shows a schematic view of an example embodiment of an inventive image data processing unit.

DETAILED DESCRIPTION OF THE EXAMPLE EMBODIMENTS

Figure 3:
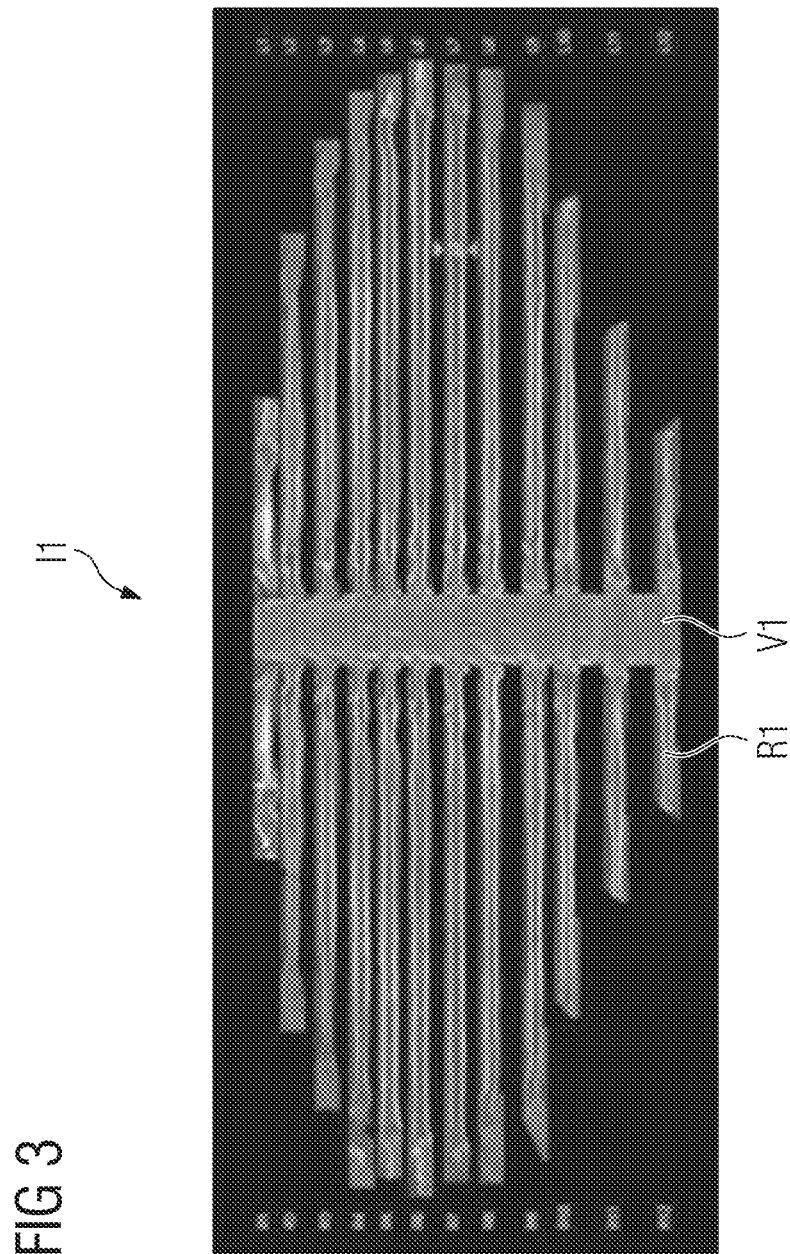
FIG. 3 shows a medical image with unfolded ribs.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Nonlimiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for image data processing, wherein the method comprising:
  providing a 3D medical image data record, which relates to an elongated anatomical structure, wherein a center line of the elongated anatomical structure is defined in the 3D medical image data record,
  defining at least one curved slice in the 3D medical image data record, wherein the at least one curved slice winds around the center line of the elongated anatomical structure,
  scanning at least one part of the 3D medical image data record into the at least one curved slice on the basis of the plurality of beams, and
  unrolling the at least one curved slice, into which the at least one part of the 3D medical image data record has been scanned, wherein at least one unrolled flat slice is determined.

In at least one embodiment, the at least one curved slice may be a plurality of curved slices.

In at least one embodiment, the curved slices of the plurality of curved slices may be arranged substantially coaxially about the center line.

In at least one embodiment, the curved slices of the plurality of curved slices may encase the center line of the elongated anatomical structure in a tubular manner in each case.

In at least one embodiment, the curved slices of the plurality of curved slices at right angles to the center line of the elongated anatomical structure may each have a circular cross-section.

In at least one embodiment, the curved slices of the plurality of curved slices may each have a cross-section which is adjusted to a surface of the elongated anatomical structure.

In at least one embodiment, the curved slices of the plurality of curved slices may each represent a surface which can be mapped by a central extension onto the surface of the elongated anatomical structure.

In at least one embodiment, the at least one curved slice can wind in the manner of a spiral around the center line of the elongated anatomical structure.

In at least one embodiment, a plurality of beams can be defined, which each run radially with respect to the center line of the elongated anatomical structure and which intersect the at least one curved slice.

In at least one embodiment, the at least one unrolled flat slice can be a plurality of unrolled flat slices, which together form a volume data record. In particular, the volume data record can represent the at least one part of the 3D medical image data record.

In at least one embodiment, a 2D image can be generated via a projection on the basis of the volume data record.

According to one embodiment of the invention, provision is made for each beam of the plurality of beams to be directed away from the center line of the elongated anatomical structure or for each beam of the plurality of beams to be directed toward the center line of the elongated anatomical structure.

According to one embodiment of the invention, the 3D medical image data record is scanned into the at least one curved slice on the basis of the plurality of beams using ray tracing and/or ray casting.

According to one embodiment of the invention, an assignment of points of the 3D medical image data record to points of the at least one unrolled flat slice or the 2D image is determined.

According to one embodiment of the invention, provision is made for the at least one part of the 3D image data record to be the 3D image data record and/or for the at least one part of the 3D image data record to be that quantity of voxels of the 3D image data record which represents a segmented partial structure of the elongated anatomical structure.

According to one embodiment of the invention, the at least one curved slice is a spiral-shaped slice, which winds around the center line of the elongated anatomical structure.

For instance, each voxel of the 3D image data record can be scanned into the spiral-shaped slice, in particular in a one-to-one manner.

A one-to-one assignment between voxels of the 3D image data records and pixels of the unrolled flat slice can therefore be realized, for instance. This prevents features, which are present in the 3D image data record, from being overlooked during diagnosis on the basis of the unrolled flat slice.

According to one embodiment of the invention, at least one partial structure of the elongated anatomical structure is segmented. In particular, the at least one part of the 3D medical image data record, which is scanned into the at least one curved slice, can be determined on the basis of the at least one partial structure. In particular, the center line of the elongated anatomical structure can firstly be determined. The elongated anatomical structure can be segmented, for instance, on the basis of the determined center line of the elongated anatomical structure. The elongated anatomical structure can be segmented, for instance, using a known method of segmentation, for instance a region growing-based method or an oval method.

The elongated anatomical structure can, in particular, be a rib and/or comprise a rib. The rib can be an unfolded rib, in particular. The rib can be unfolded for instance using a known method of rib unfolding. The elongated anatomical structure can also comprise a vertebral body.

At least one embodiment of the invention also relates to an image data processing unit, comprising:

a provisioning unit, which is embodied to provide a 3D medical image data record, which relates to an elongated anatomical structure, wherein a center line of the elongated anatomical structure is defined in the 3D medical image data record, a slice definition unit, which is embodied to define at least one curved slice in the 3D medical image data record, wherein the at least one curved slice winds around the center line of the elongated anatomical structure, a beam definition unit, which is embodied to define a plurality of beams, which each run radially with respect to the center line of the elongated anatomical structure and which intersect the at least one curved slice, a scanning unit, which is embodied to scan at least one part of the 3D medical image data record into the at least one curved slice on the basis of the plurality of beams, and an unrolling unit, which is embodied to unroll the at least one curved slice, into which the at least one part of the 3D medical image data record has been scanned, wherein at least one unrolled flat slice is determined.

According to one embodiment of the invention, the image data processing unit has a beam definition unit, which is embodied to define a plurality of beams, which each run radially with respect to the center line of the elongated anatomical structure and which intersect the at least one curved slice.

At least one embodiment of the invention also relates to a medical imaging apparatus, having the image data processing unit.

At least one embodiment of the invention further relates to a computer program product with a computer program, which can be loaded directly into a storage facility of an image data processing unit of a medical imaging apparatus, having program portions, in order to execute all the steps of an inventive method when the computer program is executed in the image data processing unit of the medical imaging apparatus.

At least one embodiment of the invention further relates to a computer-readable medium, on which program portions which can be read in and executed by a computer are stored, in order to execute all steps of an inventive method when the program portions are executed by the computer.

The medical imaging apparatus can be selected from the imaging modality group, for instance, which consists of an X-ray device, a C-arm X-ray device, a computed tomography device (CT-device), a molecular imaging device (MI device), a single photon emission computed tomography device (SPECT device), a positron emission tomography device (PET device), a magnetic resonance tomography device (MR device) and combinations thereof, in particular a PET CT device and a PET MR device. The medical imaging apparatus can further have a combination of an imaging modality which is selected, for example, from the imaging modalities group, and an irradiation modality. Herein, the irradiation modality can comprise, for example, an irradiation unit for therapeutic irradiation.

Without restricting the general inventive concept, in some of the embodiments a computed tomography device is cited as an example for a medical imaging apparatus.

The image data processing unit and/or one or more components of the image data processing unit can be formed of a data processing system. The data processing system can have one or more components in the form of hardware and/or one or more components in the form of software, for instance. The data processing system can be formed at least partially of a cloud computing system, for instance.

The data processing system can be and/or have a cloud computing system, a computer network, a computer, a tablet computer, a smartphone or suchlike or combinations thereof, for instance.

The hardware can cooperate, for example, with software and/or can be configured by way of software. The software can be executed, for example, via the hardware. The hardware can be, for example, a storage system, an FPGA system (field-programmable gate array), an ASIC system (application-specific integrated circuit), a microcontroller system, a processor system and combinations thereof. The processor system can have, for example, a microprocessor and/or a plurality of cooperating microprocessors.

In at least one embodiment, one component of the image data processing unit according to one of the aspects which are disclosed in this application, which is embodied for carrying out a defined step of a method according to one of the aspects disclosed in this application, can be implemented in the form of a hardware which is configured to execute the defined step and/or which is configured to execute a computer-readable instruction such that the hardware is configurable by way of the computer-readable instruction for executing the defined step. In particular, the system can have a storage region, for example in the form of a computer-readable medium in which computer-readable instructions, for example in the form of a computer program, are stored.

A data transfer between components of the data processing system can take place, for example, via a suitable data transfer interface in each case. The data transfer interface for data transfer to and/or from a component of the data processing system can be realized at least partially in the form of software and/or at least partially in the form of hardware. The data transfer interface can be embodied, for example, for storing data in and/or for loading data from a region of the storage system, wherein one or more components of the data processing system can access this region of the storage system.

In at least one embodiment, data which relates to a medical image, for instance, in particular the 3D image data record, can be provided by the data being loaded, for instance loaded from a region of a storage system, and/or generated, for instance using a medical imaging apparatus.

The computer program can be loaded into the storage system of the data processing system and can be executed by the processor system of the data processing system. The data processing system can be embodied for instance using the computer program such that the data processing system can execute the steps of a method according to one of the embodiments which are disclosed in this application when the computer program is executed by the data processing system.

The computer program product can be the computer program, for instance, or in addition to the computer program comprise at least one additional component. The at least one additional component of the computer program product can be embodied as hardware and/or as software.

The computer program product can have a storage medium, for instance, on which at least one part of the computer program product is stored, and/or a key for authenticating a user of the computer program product, in particular in the form of a dongle. The computer program product and/or the computer program can have a cloud application program, for instance, which is embodied to distribute program portions of the computer program onto various processing units, in particular various computers, of a cloud computing system, wherein each of the processing units is embodied to execute one or more program portions of the computer program.

The computer program product according to one of the embodiments which are disclosed in this application and/or the computer program according to one of the embodiments which are disclosed in this application can be stored on the computer-readable medium, for instance. The computer-readable medium can be a memory stick, a hard disk or other data carrier, for instance, which can be detachably connected to the data processing system in particular or fixedly integrated into the data processing system. The computer-readable medium can form a region of the storage system of the data processing system, for instance.

In the context of embodiments of the invention, features which are described in relation to different embodiments of the invention and/or different claim categories (method, use, apparatus, system, arrangement, etc.) can be combined to form further embodiments of the invention. For instance a claim which relates to an apparatus can also be further developed with features which are described or claimed in conjunction with a method. Functional features of a method can herein be carried out by correspondingly configured objective components. Apart from the embodiments of the invention expressly described in this application, many further embodiments of the invention are conceivable, at which the skilled person can arrive without departing from the scope of the invention, insofar as it is defined by the claims.

The use of the indefinite article "a" or "an" does not preclude that the relevant feature can also be present a number of times. The use of the expression "have" does not preclude that the expressions linked by the expression "have" can be identical. For example, the medical imaging apparatus has the medical imaging apparatus. The use of the expression "unit" does not preclude that the subject matter to which the expression "unit" relates can have a plurality of components that are spatially separated from one another.

The example embodiment of an inventive method shown in FIG. 1 comprises the following steps:

providing P3D a 3D medical image data record 3DI, which relates to an elongated anatomical structure RX, wherein a center line of the elongated anatomical structure RX is defined in the 3D medical image data record 3DI, defining DL at least one curved slice in the 3D medical image data record 3DI, wherein the at least one curved slice winds around the center line of the elongated anatomical structure RX, defining DR a plurality of beams, which each run radially with respect to the center line of the elongated anatomical structure RX and which intersect the at least one curved slice, scanning SL at least one part of the 3D medical image data record 3DI into the at least one curved slice on the basis of the plurality of beams, unrolling UL the at least one curved slice, into which the 3D medical image data record 3DI has been scanned, wherein at least one unrolled flat slice is determined.

The example embodiment of an inventive image data processing unit 35 shown in FIG. 2 has the following components:

a provisioning unit P3D-M, which is embodied to provide P3D a 3D medical image data record 3DI, which relates to an elongated anatomical structure, wherein a center line of the elongated anatomical structure RX is defined in the 3D medical image data record 3DI, a slice definition unit DL-M, which is embodied to define DL at least one curved slice in the 3D medical image data record 3DI, wherein the at least one curved slice winds around the center line of the elongated anatomical structure RX, a beam definition unit DR-M, which is embodied to define DR a plurality of beams, which each run radially with respect to the center line of the elongated anatomical structure RX and which intersect at least one curved slice, a scanning unit SL-M, which is embodied to scan SL the 3D medical image data record 3DI into the at least one curved slice on the basis of the plurality of beams, an unrolling unit UL-M, which is embodied to unroll UL the at least one curved slice, into which the 3D medical image data record 3DI was scanned, wherein at least one unrolled flat slice is determined.

The elongated anatomical structure RX can be an unfolded rib, in particular. FIG. 3 shows a medical image I1 with unfolded ribs R1. 24 unfolded ribs are typically present on an image. A sectional image of the rib is shown with a sectional plane, in each case. This sectional plane can be rotated with the aid of a computer mouse wheel, for instance. For a complete diagnosis, approx. 90 images must therefore generally be assessed with 24 ribs, in each case.

On the basis of the extracted center lines of the ribs R1 and/or the geometry of the associated vertebral bodies V1, the individual ribs T1 or vertebral bodies V1 can be segmented by way of a region growing-based method, for instance. Alternatively, the bones can also be segmented by way of an oval method, in which beams run from the outside in the direction of the center line CL and stop upon contact with the bone. On account of the gray scale value profile, the rib can be divided into two regions, on the one hand, into the inner region AS and on the other hand into an outer region AC. In particular, the inner region AS can correspond anatomically to the cancellous bone and the outer region AC can correspond anatomically to the cortical bone. The contour ES marks the transition between the inner region AS and the outer region AC.

The scanning SL can take place in particular by way of one of two ray tracing methods, which are explained below. These are referred to below as radial and adaptive ray tracing. Here the definition DR of the plurality of beams PR forms an optional auxiliary means, in order to scan the at least one part of the 3D image data record 3DI into the at least one curved slice. The scanning SL can also take place using other approaches, in particular without defining DR a plurality of beams PR in advance.

Figure 4:
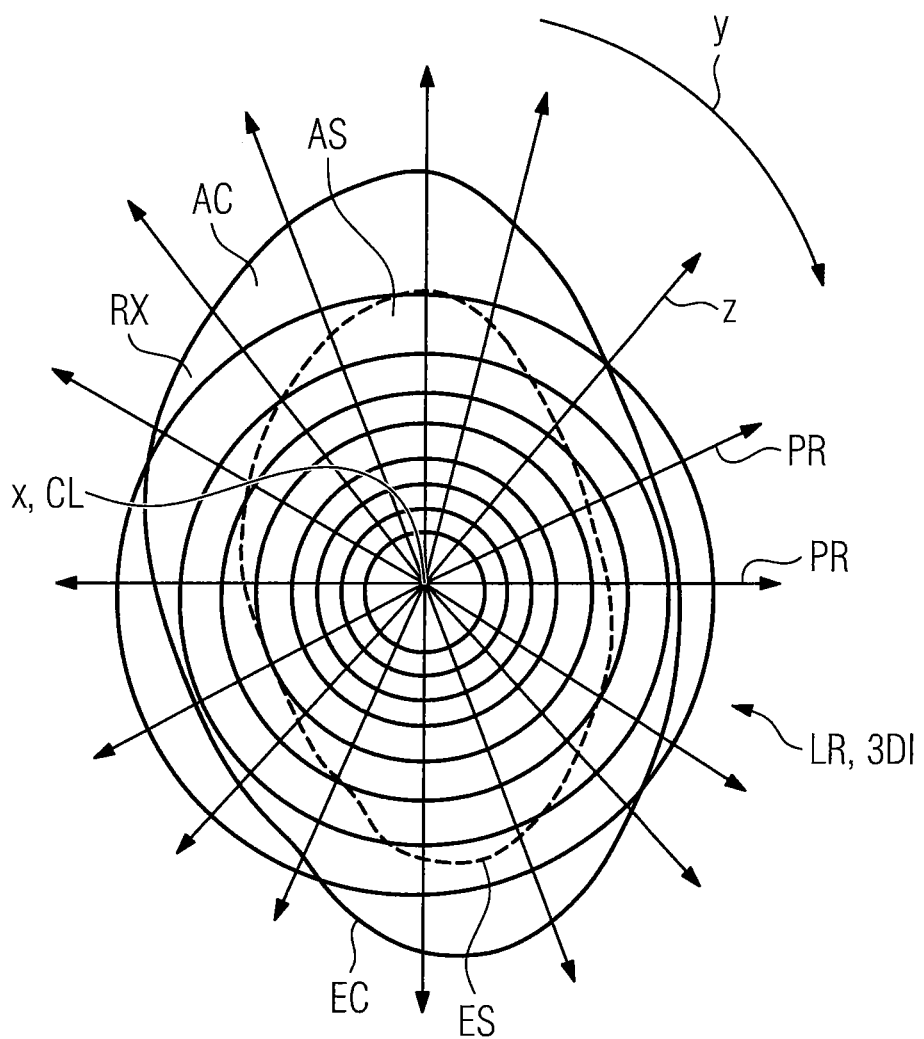
FIG. 4 shows a schematic view of a cross-section of an example of an elongated anatomical structure and at least one curved slice.

With radial ray tracing, which is shown in FIG. 4, samples are scanned radially into the respective curved slice LR, while retaining the distance from the center which is disposed on the center line CL. The resulting gray scale value image can be calculated by scanning the original image along the surface of the ribs into the at least one curved slice, which thus forms a projection surface. In such cases the center line CL of the rib is plotted onto the X-axis. Here the two selectable parameters are the number of scanned angles and the scanning rate. These can be clearly mapped onto the Y-axis and Z-axis of a three-dimensional volume via a projection rule.

Figure 5:
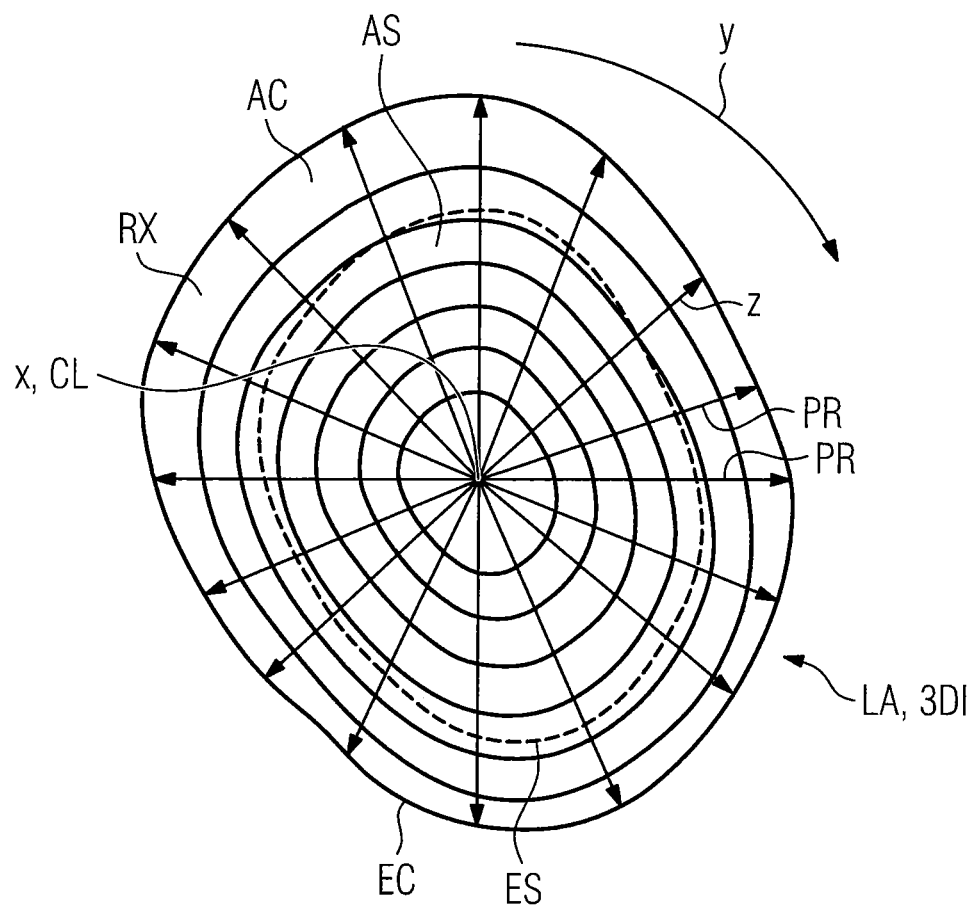
FIG. 5 shows a schematic view of a cross-section of a further example of an elongated anatomical structure and at least one curved slice.

The second method is the adaptive ray tracing method, which is shown in FIG. 5. To this end, the sampling distance along the beam is adjusted to the thickness of the rib, which equates the scanning or the curved slices LA to the surface structure of the rib. The surface EC of the rib is determined via a threshold value-based method (HU). The scanning/transmission of the density values into the folded image begins as soon as a certain HU threshold is reached. To improve and safeguard against noise, 2 or more pixels in a specific sequence can also be used to determine the surface.

Figure 6:
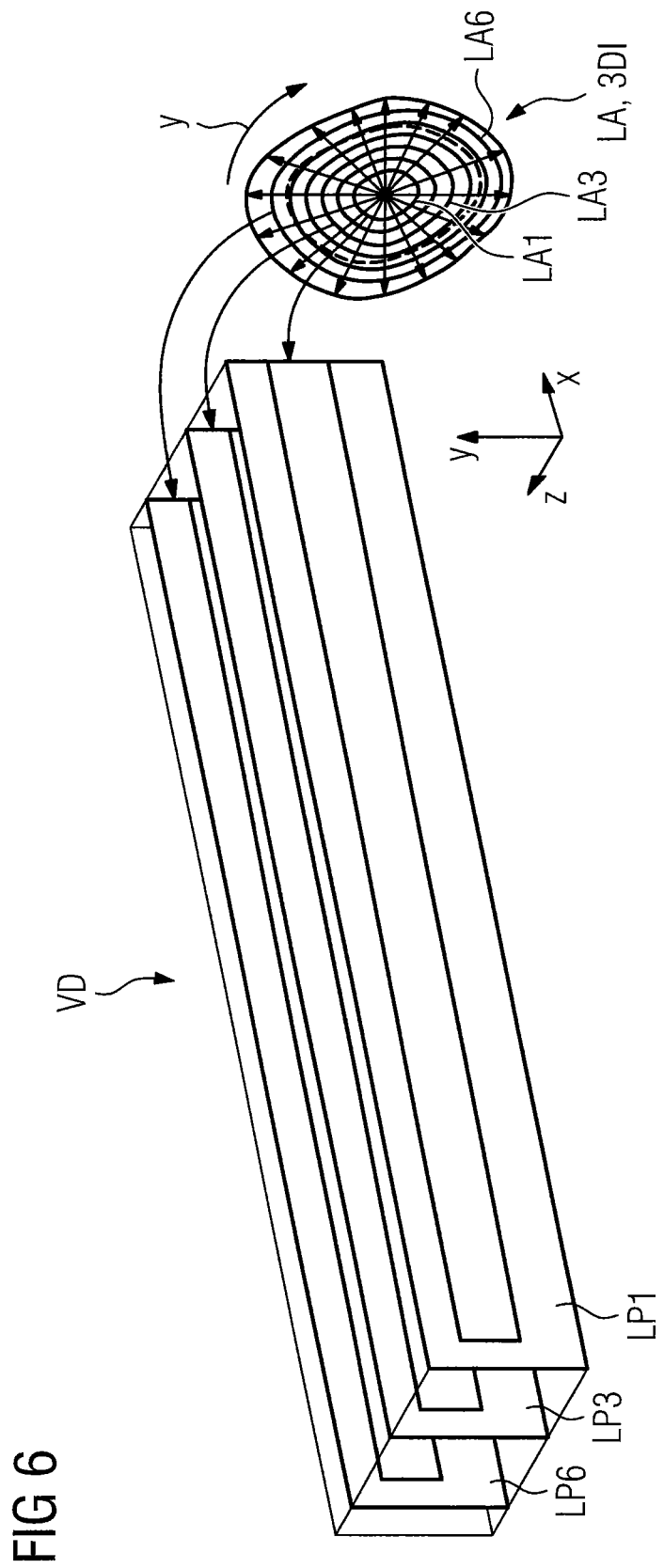
FIG. 6 shows a schematic representation of the unrolling of curves slices into flat slices.

During unrolling, as shown in FIG. 6, each curved slice LA1, LA3, LA6 is moved into a flat slice LP1, LP3, LP6. Viewed from the inside out, the first slice LA1 is disposed in the center and the last slice is disposed on the surface of the elongated anatomical structure RX, said slices being strung together along the Z-axis in the volume data record VD. Each scanned angle is plotted accordingly onto the Y-coordinate, wherein the X-axis describes the center line of the respective elongated anatomical structure RX.

Figure 7:
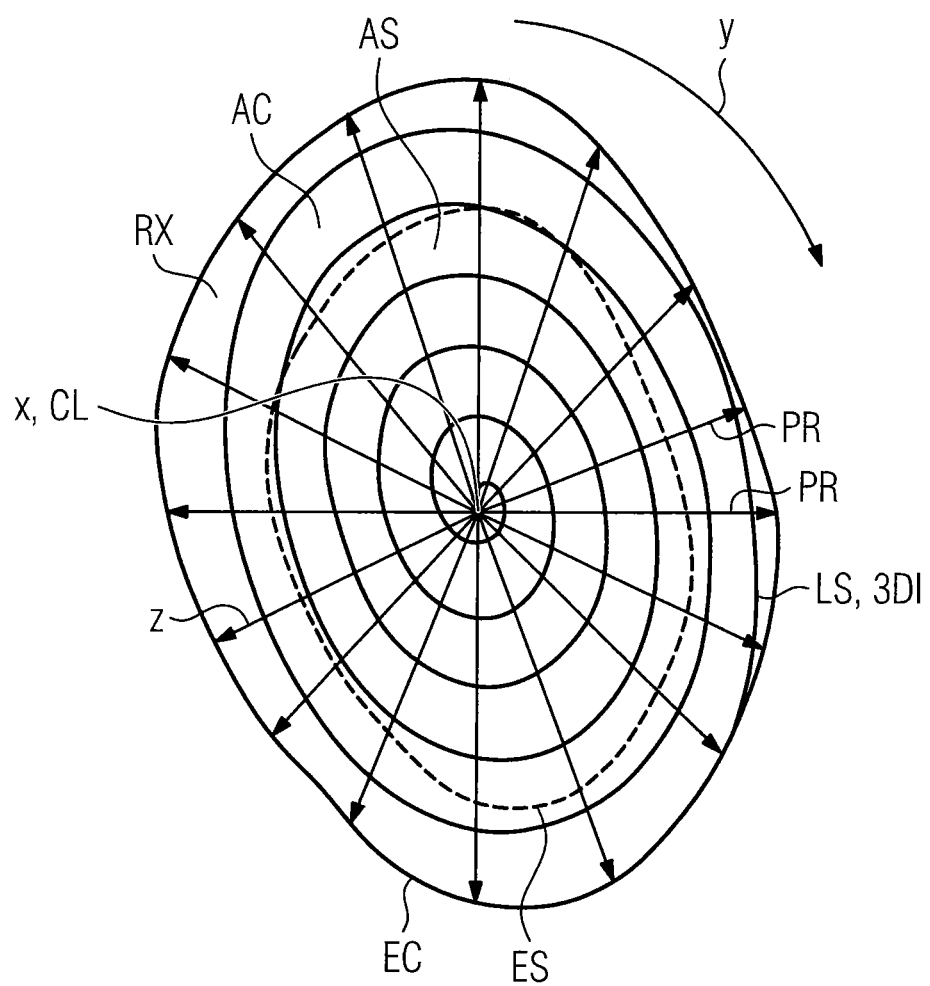
FIG. 7 shows a schematic view of a cross-section of a further example of an elongated anatomical structure and at least one curved slice.
Figure 8:
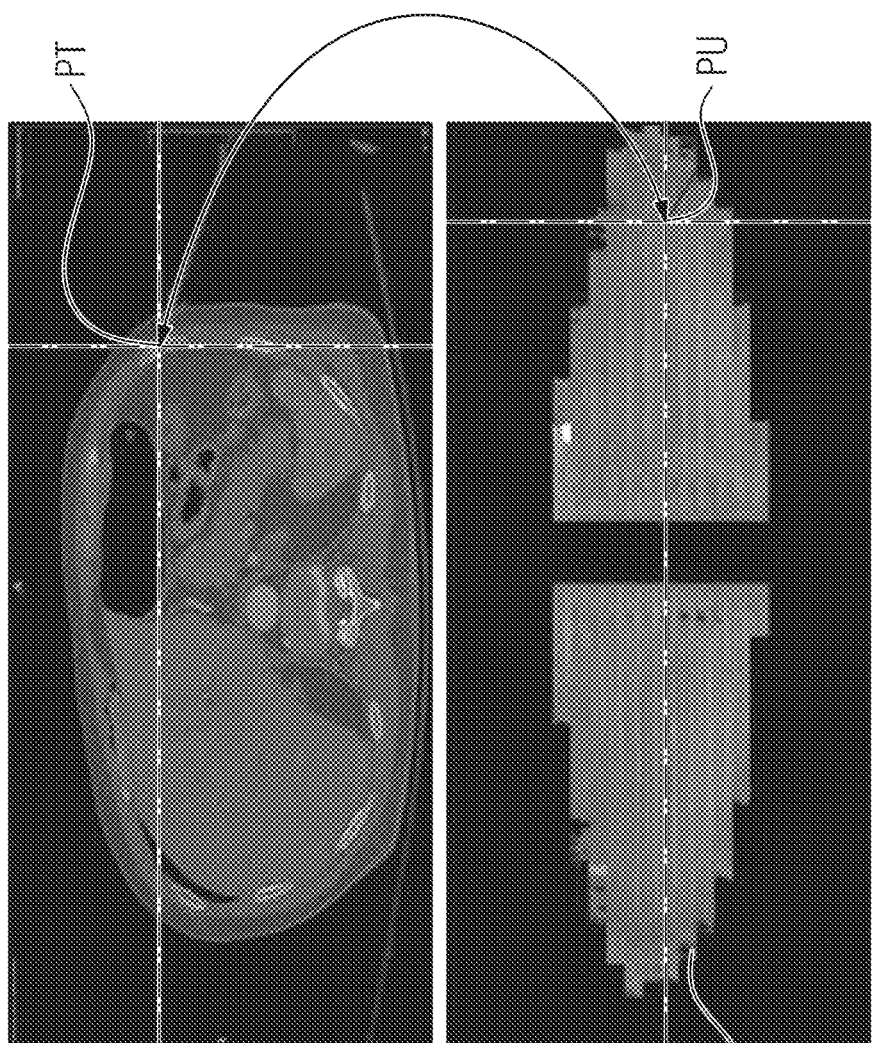
FIG. 8 shows a schematic representation of the assignment of points of the 3D medical image data record to points of the at least one unrolled flat slice or the 2D image.

A further possibility is an adaptive spiral-shaped ray casting method, which is shown in FIG. 7. To this end the sampling distance is adjusted accordingly. The scanning is carried out in a spiral shape into the curved slice LS, which winds in the manner of a spiral around the center line CL of the elongated anatomical structure RX. This is advantageous in that a volume data record is no longer generated as an intermediate step, but a dimension reduction is instead generated directly onto a 2D image. The X-axis here describes the center line of the bone and the Y-axis is determined by the spiral-shaped sampling sequence.

For the 2D display of several adjacent ribs with the aid of the respective unrolled flat slices, which have been determined in each case on the basis of the spiral-shaped slice, a portrait monitor is particularly advantageous since these unrolled flat slices have a relatively large extension in the direction of the Y-axis.

On the basis of the at least one unrolled flat slice, in particular on the basis of the volume data record, a 2D image can be generated by projections, in particular using different filters, such as e.g. minimum, maximum intensity projection or averaging. On the basis of the previously determined segmentation of the respectively hard and soft bone regions, the projection can be calculated separately or together for both segments, in each case. This separation allows 2D displays of the two regions to be generated, by e.g. different filters such as e.g. minimum, maximum intensity projection or averaging being applied to the at least one unrolled flat slice, in particular to the volume data record VD.

Bone fractures are as a result more easily visible in the minimum intensity projection (MinIP) of the cortical bone, while e.g. osteoplastic bone lesions are visible in the maximum intensity projection (MIP) of the cancellous bone.

The 2D display allows for a rapid orientation and detection of abnormalities. For detailed diagnosis in the original 3D image data, a synchronized back calculation of a marked pixel PU in the result image IU of the unrolled rib R8 is carried out with respect to the original data record position PT. This position PT is marked in the multi planar reformation (MPR) views IT by reference lines. The synchronized back calculation in the original 3D image data allows for an efficient navigation to the original data for a detailed diagnosis.

Figure 9:
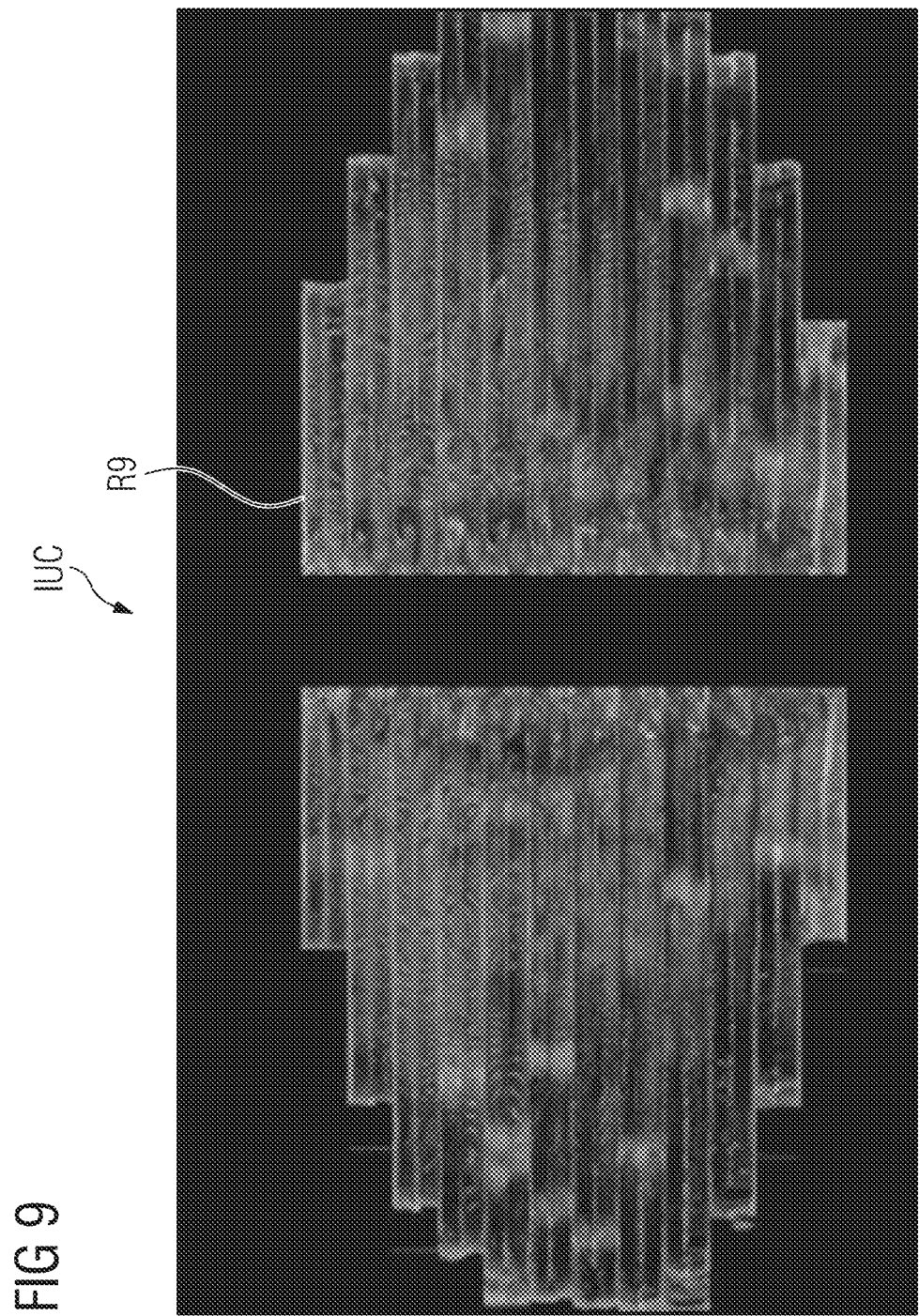
FIG. 9 shows a 2D image, which has been generated via an embodiment of the inventive method and which is shown using cinematic rendering.

Furthermore, cinematic rendering can be used to display the 2D image, which has been generated on the basis of the at least one unrolled flat slice. Cinematic rendering can be used in addition to the filters to make a lighting model available. FIG. 9 shows an example of the use of cinematic rendering in a 2D image IUC, which has been generated with the aid of the inventive method. By illuminating the images, for instance from the rear, abnormalities in the images, in particular fractures of the ribs R9, can be highlighted more clearly.

Figure 10:
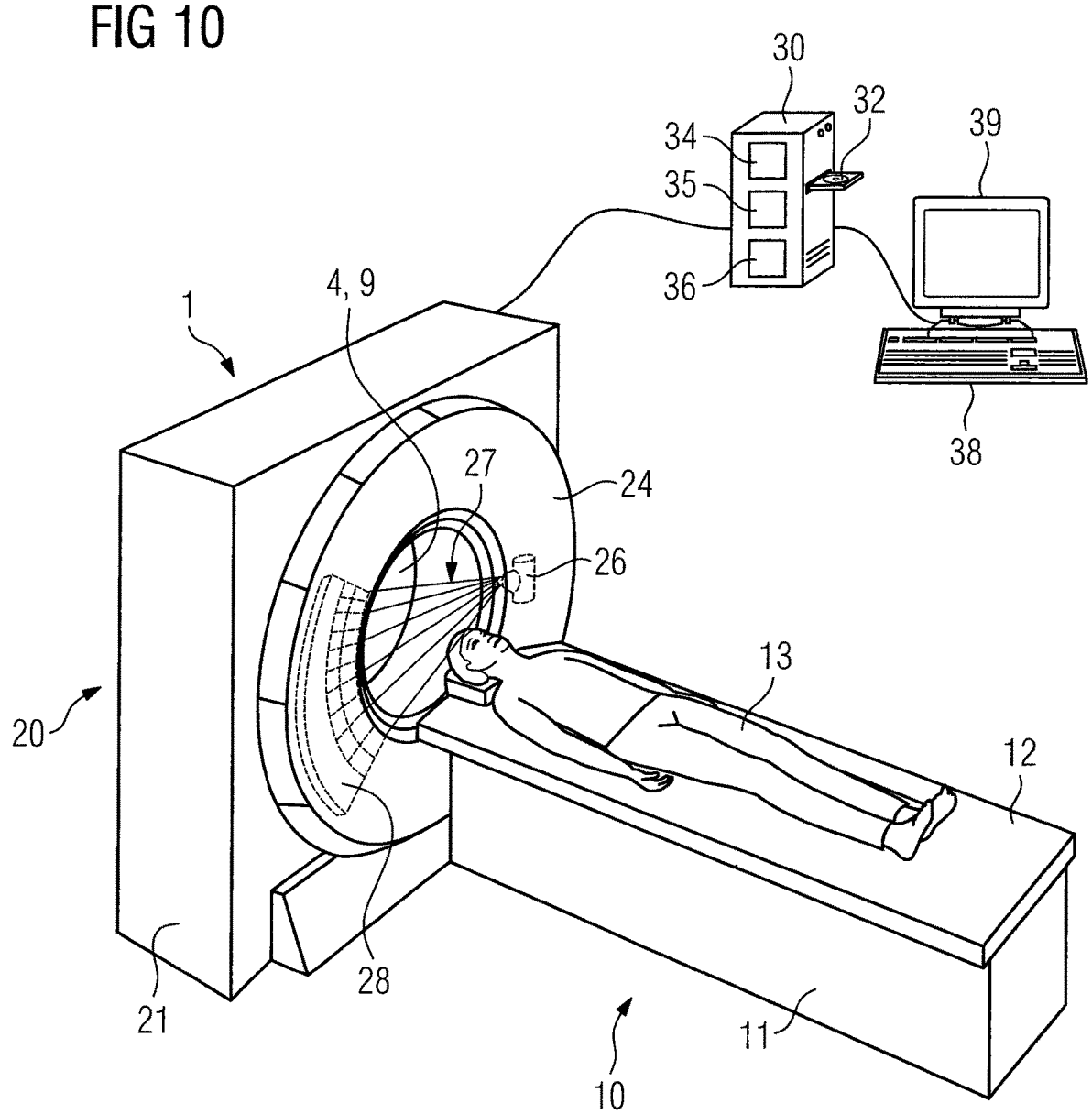
FIG. 10 shows a schematic view of an example embodiment of an inventive medical imaging apparatus.

FIG. 10 shows a schematic view of an example embodiment of an inventive medical imaging apparatus 1. Without restricting the general inventive concept, a computed tomography device is shown by way of example for the medical imaging apparatus 1. The medical imaging apparatus 1 has the gantry 20, the tunnel-shaped opening 9, the patient positioning apparatus 10 and the control apparatus 30.

The gantry 20 has the stationary support frame 21 and the rotor 24. The rotor 24 is arranged on the stationary support frame 21 so as to be rotatable about a rotation axis relative to the stationary support frame 21 via a pivot bearing apparatus. The patient 13 can be introduced into the tunnel-shaped opening 9. The acquisition region 4 is situated in the tunnel-shaped opening 9. A region of the patient 13 that is to be imaged can be positioned in the acquisition region 4 such that the radiation 27 can pass from the radiation source 26 to the region to be imaged and, following an interaction with the region to be imaged, can arrive at the radiation detector 28.

The patient positioning apparatus 10 has the positioning base 11 and the positioning table 12 for positioning the patient 13. The positioning table 12 is arranged movably on the positioning base 11 relative to the positioning base 11 such that the positioning table 12 can be introduced in a longitudinal direction of the positioning table 12, in particular along the system axis AR, into the acquisition region 4.

The medical imaging apparatus 1 is embodied for the acquisition of acquisition data on the basis of an electromagnetic radiation 27. The medical imaging apparatus 1 has an acquisition unit. The acquisition unit is a projection data acquisition unit with the radiation source 26, for example an X-ray source, and the detector 28, for example an X-ray detector, in particular an energy-resolving X-ray detector.

The radiation source 26 is arranged on the rotor 24 and is embodied for the emission of a radiation 27, for example an X-ray radiation with radiation quanta 27. The detector 28 is arranged on the rotor 24 and is configured for the detection of the radiation quanta 27. The radiation quanta 27 can pass from the radiation source 26 to the region of the patient 13 that is to be imaged and, following an interaction with the region to be imaged, can arrive at the detector 28. In this way, via the acquisition unit, acquisition data of the region to be imaged can be acquired in the form of projection data.

The control apparatus 30 is embodied for receiving the acquisition data acquired by the acquisition unit. The control apparatus 30 is embodied to control the medical imaging apparatus 1. The control apparatus 30 has the image data processing unit 35, the computer-readable medium 32 and the processor system 36. The control apparatus 30, in particular the image data processing unit 35, is formed of a data processing system, which has a computer.

The control apparatus 30 has the image reconstruction apparatus 34. Via the image reconstruction apparatus 34, on the basis of the acquisition data, a medical image data record, in particular 3D image data record 3DI, can be reconstructed. The medical imaging apparatus 1 has an input apparatus 38 and an output apparatus 39 which are each connected to the control apparatus 30. The input apparatus 38 is embodied for the input of control information, for example image reconstruction parameters, examination parameters or the like. The output apparatus 39 is embodied, in particular, for the output of control information, images and/or acoustic signals.

Embodiments of an inventive solution allows, in at least one embodiment, a method of rib unfolding to be realized, such that a dimension reduction from 3D to 2D is permitted. The ribs can therefore be visualized via a relatively compact 2D display. In particular, bone compartments, for instance cortical and cancellous bone, can be displayed intuitively in each case in a separate volume data record, which comprises unrolled flat slices. Furthermore, a 2D image can be generated via a projection method (e.g. maximum, minimum intensity projection or averaging) on the basis of the volume data record. In particular, the cancellous and cortical bone can therefore be shown in a 2D image completely separately from one another.

Basically embodiments of this method can be used applied to any elongated and/or tubular structures. It allows, in particular, various layers of such structures to be displayed separately and very compactly. Embodiments of an inventive solution allows, in particular, the cortical restriction of all ribs to be visualized on a single 2D image and/or the cortical bone (hard) and the cancellous part (soft) to be displayed separately from one another. Fractures, metastases, bone lesions, etc. can be diagnosed easily and quickly.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method, comprising:
    defining a plurality of curved slices in a 3D medical image data record, the 3D medical image data record relating to an elongated anatomical structure, a center line of the elongated anatomical structure being defined in the 3D medical image data record, the plurality of curved slices winding around the center line of the elongated anatomical structure, the plurality of curved slices including a first curved slice and a second curved slice, the first curved slice being in a cancellous bone, and the second curved slice being in a cortical bone;
    scanning at least one part of the 3D medical image data record into the plurality of curved slices based on a plurality of rays, each of the plurality of rays originating at the center line, and a sampling distance of the scanning along each respective ray among the plurality of rays being adjusted to a thickness of the elongated anatomical structure along the respective ray; and
    unrolling the plurality of curved slices after the scanning, at least one unrolled flat slice being determined from the plurality of curved slices based on the unrolling.

2. The method of claim 1, wherein the plurality of curved slices encase the center line of the elongated anatomical structure in a tubular manner.

3. The method of claim 1, wherein each curved slice of the plurality of curved slices includes a circular cross-section at right angles to the center line of the elongated anatomical structure.

4. The method of claim 3, wherein the plurality of curved slices encase the center line of the elongated anatomical structure in a tubular manner.

5. The method of claim 1, wherein each curved slice of the plurality of curved slices includes a cross-section adjusted to a surface of the elongated anatomical structure.

6. The method of claim 1, wherein each curved slice of the plurality of curved slices represents a surface, mappable onto the surface of the elongated anatomical structure via a central extension.

7. The method of claim 1, further comprising:
defining the plurality of rays, each ray of the plurality of rays intersecting the plurality of curved slices.

8. The method of claim 1, wherein the at least one unrolled flat slice includes a plurality of unrolled flat slices, the plurality of unrolled flat slices together forming a volume data record.

9. The method as claimed in claim 8, wherein a 2D image is generated via a projection based upon the volume data record.

10. The method as claimed in claim 1, wherein the scanning scans the at least one part of the 3D medical image data record into the plurality of curved slices using ray tracing or ray casting.

11. The method as claimed in claim 1, wherein the scanning scans the at least one part of the 3D medical image data record into the plurality of curved slices using adaptive ray casting or adaptive ray tracing.

12. The method as claimed in claim 11, wherein the scanning comprises adjusting the sampling distance of the scanning along each respective ray among the plurality of rays to the thickness of the elongated anatomical structure along the respective ray.

13. The method as claimed in claim 1, wherein each of the plurality of rays is radial to the center line.

14. The method as claimed in claim 13, wherein the plurality of rays includes a first ray and a second ray, a first sampling distance of the scanning along the first ray being shorter than a second sampling distance of the scanning along the second ray, and the thickness of the elongated anatomical structure being smaller along the first ray than along the second ray.

15. The method as claimed in claim 1, wherein the plurality of rays includes a first ray and a second ray, a first sampling distance of the scanning along the first ray being shorter than a second sampling distance of the scanning along the second ray.

16. The method as claimed in claim 15, wherein the thickness of the elongated anatomical structure is smaller along the first ray than along the second ray.

17. The method as claimed in claim 1, wherein a cross-section of the elongated anatomical structure perpendicular to the center line is non-circular.

18. An apparatus, comprising:
processing circuitry configured to cause the apparatus to
define a plurality of curved slices in a 3D medical image data record, the 3D medical image data record relating to an elongated anatomical structure, a center line of the elongated anatomical structure being defined in the 3D medical image data record, the plurality of curved slices winding around the center line of the elongated anatomical structure, the plurality of curved slices including a first curved slice and a second curved slice, the first curved slice being in a cancellous bone, and the second curved slice being in a cortical bone,
scan at least one part of the 3D medical image data record into the plurality of curved slices based on a plurality of rays, each of the plurality of rays originating at the center line, and a sampling distance of the scan along each respective ray among the plurality of rays being adjusted to a thickness of the elongated anatomical structure along the respective ray, and
unroll the plurality of curved slices into which the at least one part of the 3D medical image data record has been scanned, and at least one unrolled flat slice being determined from the plurality of curved slices once unrolled.

19. The apparatus of claim 18, wherein the apparatus is a medical imaging apparatus.

20. The apparatus of claim 18, wherein a cross-section of the elongated anatomical structure perpendicular to the center line is non-circular.

21. A method, comprising:
defining a plurality of curved slices in a 3D medical image data record, the 3D medical image data record relating to an elongated anatomical structure, a center line of the elongated anatomical structure being defined in the 3D medical image data record, the plurality of curved slices winding around the center line of the elongated anatomical structure, the plurality of curved slices including a first curved slice and a second curved slice, the first curved slice being in a cancellous bone, and the second curved slice being in a cortical bone;
scanning at least one part of the 3D medical image data record into the plurality of curved slices based on a plurality of rays, each of the plurality of rays originating at the center line, and a sampling distance of the scanning along each respective ray among the plurality of rays being adjusted to a thickness of the elongated anatomical structure along the respective ray; and
determining at least one unrolled flat slice from the plurality of curved slices after the scanning.

22. The method as claimed in claim 21, wherein a cross-section of the elongated anatomical structure perpendicular to the center line is non-circular.

* * * * *